(12) United States Patent
Haslbeck et al.

(10) Patent No.: US 11,083,839 B2
(45) Date of Patent: Aug. 10, 2021

(54) INFUSION ARRANGEMENT FOR ADMINISTERING A MEDICAL FLUID

(71) Applicant: B. BRAUN MELSUNGEN AG, Melsungen (DE)

(72) Inventors: Karsten Haslbeck, Melsungen (DE); Jens Wildhagen, Hannover (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 100 days.

(21) Appl. No.: 16/505,876

(22) Filed: Jul. 9, 2019

(65) Prior Publication Data

US 2020/0016332 A1 Jan. 16, 2020

(30) Foreign Application Priority Data

Jul. 10, 2018 (DE) .................... 10 2018 211 392.0

(51) Int. Cl.
*A61M 5/145* (2006.01)
*A61M 5/168* (2006.01)

(52) U.S. Cl.
CPC .... *A61M 5/14586* (2013.01); *A61M 5/16886* (2013.01); *A61M 2205/0216* (2013.01);
(Continued)

(58) Field of Classification Search
CPC .......... A61M 5/14586; A61M 5/14244; A61M 2205/3331; A61M 5/172;
(Continued)

(56) References Cited

U.S. PATENT DOCUMENTS

2005/0267413 A1* 12/2005 Wang ................ A61M 5/16831
604/131
2009/0113996 A1 5/2009 Wang et al.
(Continued)

FOREIGN PATENT DOCUMENTS

DE 19853035 A1 5/2000
DE 10249238 A1 5/2004
(Continued)

OTHER PUBLICATIONS

German Search Report for German Application No. 10 2018 211 392.0, dated Oct. 12, 2018—8 pages.
Extended European Search Report for European Application No. 19 177 873.7, dated Nov. 18, 2019, 7 pages.

*Primary Examiner* — Kami A Bosworth
*Assistant Examiner* — Emily J Becker

(57) ABSTRACT

An infusion arrangement for administering a medical fluid includes a pump apparatus with an elastomeric membrane which forms a pump volume. The elastomeric membrane is elastically extended in a fill state, filled at least partially with medical fluid, of the pump volume and produces a delivery pressure on the pump volume. An infusion line is connected to the pump volume and provided with a patient access for fluid-conducting connection. A main fluid channel transfers medical fluid from the pump volume to the patient access. A monitoring device is connected to the infusion line and configured for monitoring the pump apparatus. The monitoring device has a differential pressure-measuring element connected to the main fluid channel and designed such that differential pressure formed along a channel portion of the main fluid channel can be detected by the differential pressure-measuring element and a delivery rate of the medical fluid can be indicated.

20 Claims, 2 Drawing Sheets

Figure 1:
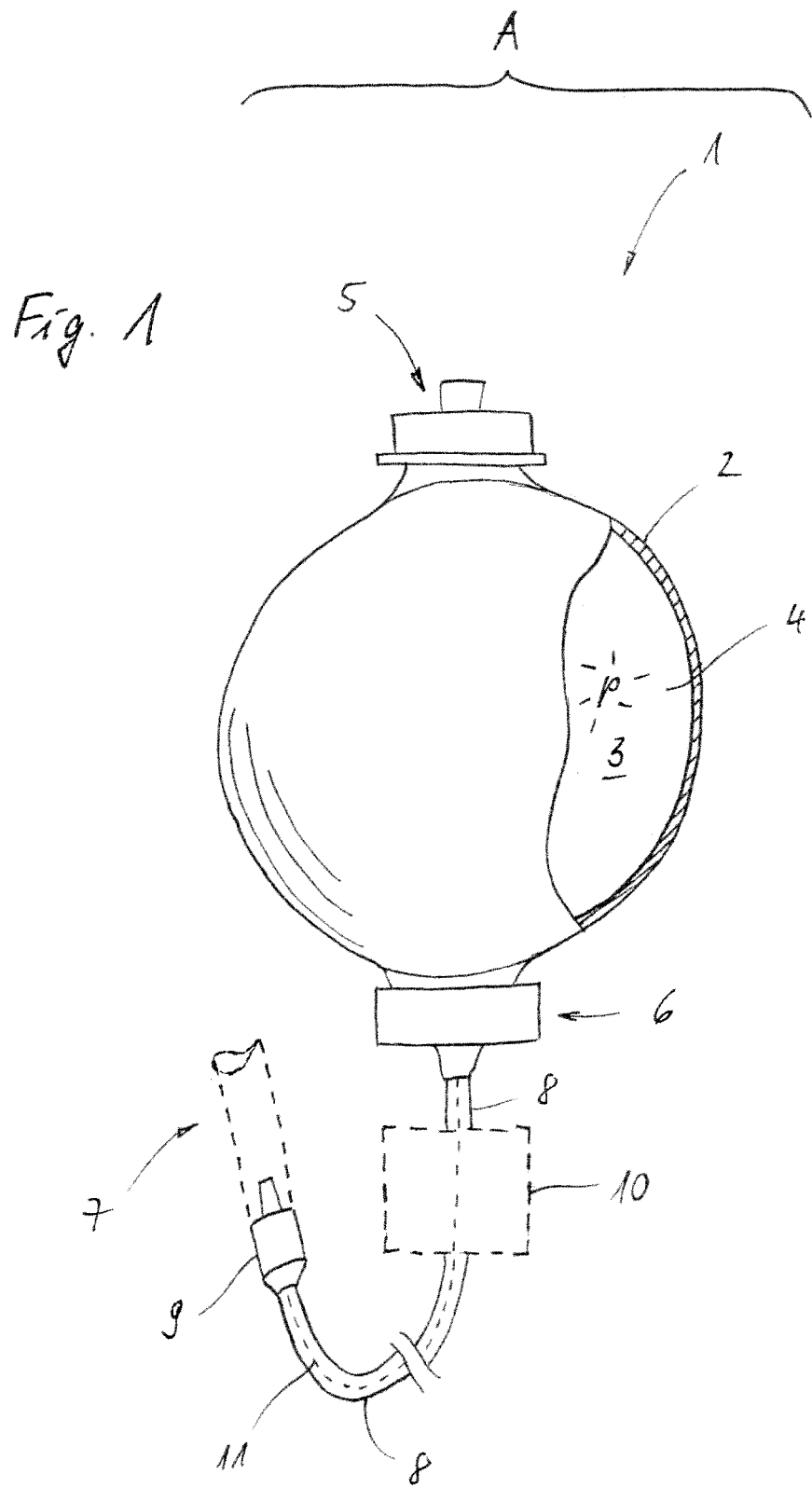

(52) U.S. Cl.
CPC ............... *A61M 2205/3331* (2013.01); *A61M 2205/583* (2013.01)

(58) Field of Classification Search
CPC ...... A61M 2205/0216; A61M 5/16804; A61M 5/16886; A61M 5/14224; A61M 5/16809; A61M 2205/8206; A61M 2205/581; A61M 2205/583; A61M 5/16854; A61M 5/16859; A61M 5/16881; A61M 2205/3337; A61M 2205/3348; A61M 2205/3355; A61M 5/1723; A61M 5/14593; A61M 5/1483; A61M 2205/3334; A61M 5/152
See application file for complete search history.

(56) References Cited

U.S. PATENT DOCUMENTS

| | | | |
|---|---|---|---|
| 2009/0157040 A1 | 6/2009 | Jacobson et al. | |
| 2010/0191223 A1* | 7/2010 | Togawa ................ | A61M 5/168 604/892.1 |
| 2013/0218133 A1* | 8/2013 | Barclay ................ | A61M 5/172 604/518 |
| 2017/0000945 A1 | 1/2017 | Haslbeck | |

FOREIGN PATENT DOCUMENTS

| | | | |
|---|---|---|---|
| EP | 0337092 | A2 | 10/1989 |
| WO | 2015110387 | A1 | 7/2015 |

* cited by examiner

INFUSION ARRANGEMENT FOR ADMINISTERING A MEDICAL FLUID

RELATED APPLICATION(S)

This application claims the benefit of priority under 35 U.S.C. § 119 of German Application No. 10 2018 211 392.0, filed Jul. 10, 2018, the contents of which is incorporated by reference herein in its entirety.

FIELD

The invention relates to an infusion arrangement for administering a medical fluid, having a medical pump apparatus with an elastomeric membrane which forms a pump volume for receiving and delivering the medical fluid, wherein the elastomeric membrane is elastically extended in a fill state, filled at least partially with the medical fluid, of the pump volume and thereby produces a delivery pressure on the pump volume, and having an infusion line which, at one end, is operatively connected to the pump volume and which, at the other end, is provided with a patient access means for fluid-conducting connection and which forms a main fluid channel for transferring the medical fluid from the pump volume to the patient access means, and having a mechanical monitoring device which is operatively connected to the infusion line and which is configured for monitoring the functioning of the pump apparatus.

BACKGROUND

Such an infusion arrangement is known from WO 2015/110387 A1 and is provided for administering a medical fluid in the context of infusion therapy. The known infusion arrangement has a medical pump apparatus which is in the form of a medical elastomer pump having a membrane, said membrane being able to be elastically extended like a balloon and serving for receiving and delivering the medical fluid. Moreover, the known infusion arrangement has an infusion line which is operatively connected to a pump volume of the membrane. The infusion line forms a main fluid channel for transferring the medical fluid from the pump volume to a patient access means. For the purpose of monitoring the functioning of the pump apparatus, the known infusion arrangement has a mechanical monitoring device. The monitoring device has a measurement reservoir which is connected in fluid-conducting fashion to the main fluid channel by means of a channel branch. For the purpose of monitoring the functioning, the main fluid channel is manually clamped off behind the channel branch by means of a clamp. When the pump apparatus is functioning correctly, this brings about an increase in pressure in the main fluid channel, which leads to a pressure-driven flow of medical fluid into the measurement reservoir. By contrast, if the pump is not functioning or if the main fluid channel is blocked in front of the channel branch, no medical fluid passes into the measurement reservoir. A user can thereby infer the functional capability of the pump apparatus in a manner dependent on whether medical fluid flows into the measurement reservoir or not. Consequently, for the known infusion arrangement, the monitoring of the functioning constantly requires a temporary interruption to the administration of fluid. Furthermore, the monitoring of the functioning provides merely purely qualitative information, specifically whether a pump delivery is taking place or not.

SUMMARY

It is an object of the invention to provide an infusion arrangement of the type mentioned in the introduction which allows improved monitoring of the functioning of the pump apparatus, wherein in particular, the intention is that interruption to administration of fluid is avoided and quantitative information with regard to the delivery functioning of the pump apparatus is made possible.

Said object is achieved in that the monitoring device has a differential pressure-measuring element operatively connected to the main fluid channel and is designed such that a differential pressure formed along a channel portion of the main fluid channel is able to be detected by means of the differential pressure-measuring element and, in a manner dependent on the differential pressure, a delivery rate of the medical fluid along the main fluid channel is able to be indicated. The solution according to the invention allows a differential pressure-dependent monitoring of the functioning during a running delivery operation of the pump apparatus, and thus an interruption-free, continuous administration of fluid. In this way, temporary interruption of the main fluid channel and thus temporary interruption of the infusion therapy can be rendered unnecessary. The differential pressure-measuring element serves for detecting the differential pressure formed along the channel portion. Such a pressure difference can be formed owing to friction-induced flow losses, which are inevitably present, and/or owing to a fluid-throttling element arranged in the channel portion. By contrast, if a malfunction of the pump apparatus is present or if the channel portion is blocked, no medical fluid flows through the channel portion and, consequently, no such pressure difference is formed. Here, the monitoring device is configured such that, in a manner dependent on the differential pressure determined by means of the differential pressure-measuring element, the delivery rate of the medical fluid along the main fluid channel is able to be indicated. The delivery rate may also be referred to as the volumetric flow rate, mass flow rate or throughflow rate. The monitoring device thus allows qualitative information with regard to the delivery function of the pump apparatus. Consequently, in addition to performing basic monitoring of the pump function, a user of the infusion arrangement can also monitor the delivery rate of the medical fluid. In this way, insufficient and/or excessive dosing of the medical fluid is avoided, this ultimately allowing improved infusion therapy and increased patient safety. The mechanical monitoring device is preferably designed such that an external energy supply can be dispensed with. The medical pump apparatus is preferably in the form of a medical elastomer pump generally known in the field of medical technology, which may also be referred to as an elastomeric infusion pump. The elastomeric membrane forms the pump volume and thus a kind of cavity. Thus, the elastomeric membrane may also be referred to as an elastomeric hollow membrane.

In one configuration of the invention, the monitoring device has a bypass channel which is operatively connected at one end by means of a first channel branch, and at the other end by means of a second channel branch, to the main fluid channel, in each case in fluid pressure-transmitting fashion, wherein the differential pressure-measuring element is arranged in the bypass channel. The bypass channel is preferably in the form of a hose line. The channel branches may be arranged integrally on the infusion line or joined to the latter at a later stage. The channel portion is preferably extended between the first channel branch and the second channel branch. Simply put, the bypass channel serves for picking up the differential pressure between the first and second channel branches. Preferably, the bypass channel serves exclusively for detecting the differential pressure.

Provision is preferably not made for delivery of the medical fluid along the bypass channel.

In a further configuration of the invention, the differential pressure-measuring element has at least one mechanical measurement member, which is able to be deflected in resiliently elastic fashion by means of application of differential pressure. The mechanical measurement member is operatively connected in fluid pressure-transmitting fashion to the main fluid channel. If a bypass channel is provided, the mechanical measurement member is preferably operatively connected to the bypass channel in fluid pressure-transmitting fashion. The mechanical measurement member may for example be in the form of a hydraulically deflectable spring-loaded plunger, a membrane or the like.

In a further configuration of the invention, the mechanical measurement member has at least one resiliently elastic membrane. This is a particularly robust and reliable configuration of the invention.

In a further configuration of the invention, the monitoring device has an indicator element which is operatively connected to the differential pressure-measuring element and which is configured for indicating the delivery rate in a manner dependent on the differential pressure. The indicator element can be operatively connected to the differential pressure-measuring element by means of mechanical transmission. In this way, it is possible for a differential pressure-induced deflection of the differential pressure-measuring element, in particular the resiliently elastic deflection of the mechanical measurement member of the differential pressure-measuring element, to be transmitted into an indicator movement of the indicator element. The indicator element is preferably assigned a scale for reading off the delivery rate.

In a further embodiment of the invention, the monitoring device has at least one fluid-filled fluid chamber, wherein the indicator element is arranged in the fluid chamber so as to be movable in a floating manner. The fluid chamber is preferably hydraulically operatively connected to the main fluid channel. If a bypass channel is provided, the fluid chamber is preferably hydraulically connected to the bypass channel. The fluid chamber is preferably of transparent form at least portionally such that a user can view a differential pressure-induced floating movement of the indicator element within the fluid chamber.

In a further configuration of the invention, the indicator element is in the form of a float or of a dyed oil drop. Here, the dyeing of the oil drop serves for improved visual perceptibility of the respective floating position of the oil drop within the fluid chamber. This makes it possible to achieve improved readability of the monitoring device.

In a further embodiment of the invention, the monitoring device has a first fluid-throttling element arranged in the main fluid channel between the first channel branch and the second channel branch. The fluid-throttling element is thus preferably arranged within the channel portion. The fluid-throttling element serves for influencing the differential pressure. In comparison with a non-throttled configuration, in which the differential pressure is formed as a result of flow losses, which are inevitably present, within the channel portion, the fluid-throttling element brings about a relatively higher differential pressure. This allows in particular a less measurement-sensitive configuration of the differential pressure-measuring element. The fluid-throttling element may be in the form of a restriction of the channel portion or in the form of a separate fluidic structural element and introduced into the channel portion.

In a further configuration of the invention, a second fluid-throttling element is arranged in the main fluid channel downstream of the second channel branch. The second fluid-throttling element serves in particular for reducing the pressure of the medical fluid to be administered, such that said fluid can be dispensed at a predetermined starting pressure from the infusion line into the patient access means. Here, "downstream" means that the second fluid-throttling element is—in relation to an intended delivery direction of the pump apparatus—arranged behind the second channel branch. The second fluid-throttling element may be in the form of a restriction of the main fluid channel or, in the form of a separate fluidic structural element, arranged in the main fluid channel.

In a further configuration of the invention, the first fluid-throttling element has a throttling action which is lower, preferably 1.5 to 15 times lower, in comparison with the second fluid-throttling element. Accordingly, the first fluid-throttling element has a throttling action which is reduced, preferably significantly reduced, in comparison with the second fluid-throttling element. It has been found that this configuration of the invention allows particularly advantageous determinability of the delivery rate. In particular, a linearization of the delivery rate determination with respect to pressure fluctuations of the medical pump apparatus can be made possible.

BRIEF DESCRIPTION OF THE DRAWING FIGURES

Further advantages and features of the invention will emerge from the claims and from the following description of a preferred exemplary embodiment of the invention, which is illustrated on the basis of the drawings.

Figure 2:
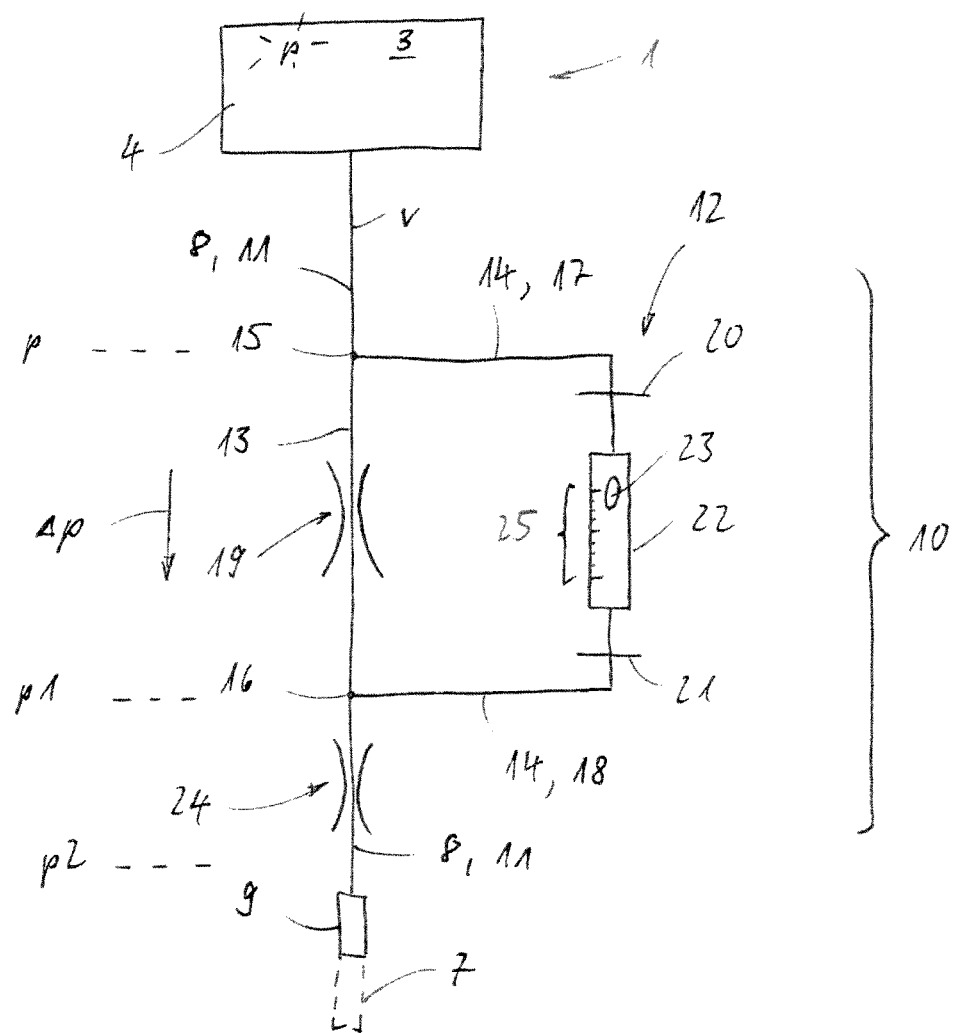

FIG. 1 shows, in a partially cut-open schematic illustration, an embodiment of an infusion arrangement according to the invention, and FIG. 2 shows the infusion arrangement as per FIG. 1 in a highly simplified schematic illustration.

DETAILED DESCRIPTION

An infusion arrangement A as per FIGS. 1 and 2 is provided for administering a medical fluid 4 in the context of outpatient and/or inpatient infusion therapy. The infusion arrangement A has a medical pump apparatus 1, which may also be referred to as an elastomeric infusion pump or medical elastomer pump. The medical pump apparatus 1 has an elastomeric membrane 2 which forms a pump volume 3 for receiving and delivering the medical fluid 4. With reference to FIG. 1, the medical pump apparatus 1 is shown in a fill state filled at least partially with the medical fluid 4. In this state, the elastomeric membrane 2 is flexibly extended like a balloon as a result of an effect of the medical fluid 4. With reference to FIG. 1, the membrane 2 is illustrated with an exaggerated wall thickness for graphic reasons. In a state not filled with medical fluid 4, the membrane 2 is, by contrast, slack or at any rate elastically extended to a lesser extent. For the purpose of filling the pump volume 3 or the membrane 2 with medical fluid 4, a reclosable filling nozzle 5 is provided, which is connected to the membrane 2 in fluid-tight fashion in a manner that is basically known.

The elastically extended membrane 2 produces a delivery pressure p on the pump volume 3. By means of the delivery pressure p produced in this manner, the medical fluid 4 is able to be delivered via an outlet nozzle 6, which is connected in fluid-tight fashion to the membrane 2, from the pump volume 3 into an infusion line 8 which, at one end, is operatively connected in fluid-conducting fashion to the pump volume 3. For this purpose, the infusion line 8 is non-releasably connected at one end, at its face end facing the pump volume 3, to the outlet nozzle 6. At its opposite face end, the infusion line 8 has a connector 9, which is in the form of a Luer connector in the present case. In one embodiment (not illustrated), the connector is in the form of an NRFit connector. The Luer connector 9 is provided for connection to a patient access means 7. With reference to FIG. 1, the patient access means 7 is illustrated merely schematically in a highly simplified manner and partially cut away. In this way, the infusion line 8 forms a main fluid channel 11 for transferring the medical fluid 4 from the pump volume 3 to the patient access means 7. With reference to FIG. 1, the main fluid channel 11 is illustrated by a dashed line in a schematic manner.

In the present case, the pump apparatus 1 is dimensioned such that it is readily worn on the body by a patient and is able to be used without an external energy supply in the context of outpatient therapy. The pump apparatus 1 is accordingly light and dimensionally compact, wherein, in the present case, the pump volume 3 has a nominal size of 400 ml. It goes without saying that the pump volume 3 may also have a different size, for example of 50 ml to 750 ml.

As can also be seen with reference to FIG. 1, the infusion arrangement A has a mechanical monitoring device 10 which is operatively connected to the infusion line 8. The monitoring device 10 is configured for monitoring the functioning of the medical pump apparatus 1 and is operatively connected to the infusion line 8 for this purpose. With reference to FIG. 1, the monitoring device 10 is indicated merely schematically. Further structural and functional features of the monitoring device 10 can be seen with reference to FIG. 2.

The monitoring device 10 has a differential pressure-measuring element 12 operatively connected to the main fluid channel 11 and is designed such that a differential pressure $\Delta p$ formed along a channel portion 13 of the main fluid channel 11 is able to be detected by means of the differential pressure-measuring element 12 and, in a manner dependent on the differential pressure $\Delta p$, a delivery rate v of the medical fluid 4 along the main fluid channel 11 is able to be indicated.

In the present case, the mechanical monitoring device 10 has a bypass channel 14 for this purpose. The bypass channel 14 is operatively connected at one end by means of a first channel branch 15, and at the other end by means of a second channel branch 16, to the main fluid channel 11, in each case in fluid pressure-transmitting fashion. In the present case, the differential pressure-measuring element 12 is arranged here in the bypass channel 14. In the present case, the bypass channel is in the form of a hose line 14 which has a first line portion 17 and a second line portion 18. The first line portion 17 establishes a fluid pressure-transmitting operative connection between the first channel branch 15 and the differential pressure-measuring element 12. The second line portion establishes a fluid pressure-transmitting operative connection between the second channel branch 16 and the differential pressure-measuring element 12. The channel portion 13 is extended between the first channel branch 15 and the second channel branch 16 on the fluid flow side.

When the medical fluid 4 is delivered by means of the medical pump apparatus 1, a pressure gradient is formed along the main fluid channel 1. Said pressure gradient can be formed, partially at any rate, by a flow resistance of the infusion line 8, which is inevitably present. Moreover, in the present case, the monitoring device 10 has a fluid-throttling element 19 arranged in the main fluid channel 11 between the first channel branch 15 and the second channel branch 16. The fluid-throttling element 19 contributes to the above-described pressure gradient and/or influences the latter to a substantial extent. In the present case, the fluid-throttling element 19 is in the form of a fluidic control element. In one embodiment (not illustrated), the fluid-throttling element may be formed integrally on the infusion line 8 in the form of a restriction of the flow cross section.

Simply put, the fluid pressure in front of and behind the fluid-throttling element 19 is picked up by means of the bypass channel 14. The delivery pressure p prevails—approximately at any rate—upstream of the fluid-throttling element 19. By contrast, a fluid pressure p1 prevails downstream of the fluid-throttling element in the region of the second channel branch 16. In this respect, the differential pressure $\Delta p$ is determined from the difference between the two aforementioned pressures p and p1.

In the present case, the differential pressure-measuring element 12 has at least one mechanical measurement member 20, 21, which is able to be deflected in resiliently elastic fashion by means of application of differential pressure. In the present case, a first measurement member 20 and a second measurement member 21 are provided here. The first measurement member 20 is arranged at the face-end side of the first line portion 17. The second measurement member 21 is arranged at the face-end side of the second line portion 18. The measurement members 20, 21 are each operatively connected in fluid pressure-transmitting fashion to the bypass channel 14 and are each in the form of a resiliently elastically deflectable membrane 20, 21. The monitoring device 10 furthermore has a fluid-filled fluid chamber 22. The two membranes 20, 21 are each hydraulically coupled to the fluid chamber 22. An indicator element 23 is arranged in the fluid chamber 22 so as to be movable in a floating manner. In the present case, the indicator element is in the form of a float 23 and is configured for indicating the delivery rate v in a manner dependent on the differential pressure $\Delta p$. In one embodiment (not illustrated), the indicator element may be in the form of a dyed oil drop. The fluid chamber 22 is hydraulically operatively connected to the membranes 20, 21 such that the differential pressure $\Delta p$ detected by means of the membranes 20, 21 is able to be transmitted to the fluid situated in the fluid chamber 22, which fluid is not designated more specifically. In the present case, a fluid-conducting connection from the first channel branch 15 via the bypass channel 14 further to the second channel branch 16 is not brought about by means of the differential pressure-measuring element 12 and in particular by means of the fluid chamber 22. The fluid chamber 22 is, portionally at any rate, of transparent form. For this purpose, the fluid chamber 22 may be produced for example from a transparent plastic. In this way, a differential pressure-induced floating movement of the float 23 within the fluid chamber 22 is able to be clearly ascertained visually by a user of the infusion arrangement A for the purpose of monitoring the functioning of the pump apparatus 1. The fluid chamber 22 and/or the indicator element 23 are/is assigned a scale 25. Here, the monitoring device 10 is configured such that the float 23 is movable in a floating manner along the scale 25 in a manner dependent on the differential pressure $\Delta p$ transmitted to the fluid chamber 22 by means of the membranes 20, 21, wherein a position of the float 23 in relation to the scale 25 is in a fixed ratio to the delivery rate v.

In the present case, a second fluid-throttling element 24 is arranged in the main fluid channel 11 downstream of the second channel branch 16. Here, the throttling action of the first fluid-throttling element 19 is significantly lower than that of the second fluid-throttling element 24. Preferably, the throttling action of the first fluid-throttling element 19 is 1.5 times to 15 times lower than the throttling action of the second fluid-throttling element 24. A fluid pressure p2 prevails in the main fluid channel 11 downstream of the second fluid-throttling element 24. Said pressure corresponds to the pressure at which the medical fluid 4 is dispensed from the infusion line 8 into the patient access means 7.

For the purpose of administering the medical fluid 4, said fluid passes from the pump volume 3, pressurized by means of the elastically extended membrane 2, at the delivery pressure p into the infusion line 8 and flows along the main fluid channel 11 into the patient access means 7. Here, the medical fluid 4, proceeding from the pump volume 3, firstly passes the first channel branch 15, enters the channel portion 13, flows through the first fluid-throttling element 19, passes the second channel branch 16 and finally flows through the second fluid-throttling element 24 and the Luer lock connector 9.

When the medical pump apparatus 1 is functioning correctly, the delivery of the medical fluid 4 is realized here at the delivery rate v, wherein a pressure gradient is established along the main fluid channel 11 and, specifically, the differential pressure $\Delta p$ is formed between the channel branches 15, 16. The differential pressure $\Delta p$ is transmitted hydraulically to the fluid chamber 22 via the bypass channel 14 and by means of the membranes 20, 21. In the process, the float 23 is moved along the scale 25 in a manner dependent on the differential pressure $\Delta p$. Owing to the physical relationship between the differential pressure $\Delta p$ and the delivery rate v, the monitoring device 10 does not merely allow a statement as to whether a throughflow is present or not, but quantifies this in the form of the delivery rate v which is able to be read off the scale 25.

If, by contrast, the pump apparatus 1 is not functioning correctly and does not produce a delivery pressure p, non-delivery of the medical fluid 4 along the infusion line 8 is consequently also established. Instead, the medical fluid 4 is stationary within the main fluid channel 11. Accordingly, the differential pressure $\Delta p$ is zero. This is reflected in the position of the float 23 relative to the scale 25. A malfunction of the pump apparatus 1 and/or a delivery rate which does not comply with requirements is thereby easily able to be ascertained by a user of the infusion arrangement A.

The invention claimed is:

1. An infusion arrangement for administering a medical fluid comprising:
   a medical pump apparatus comprising an elastomeric membrane which forms a pump volume for receiving and delivering the medical fluid, wherein the elastomeric membrane is elastically extended in a fill state, filled at least partially with the medical fluid, of the pump volume and thereby produces a delivery pressure on the pump volume;
   an infusion line configured to be operatively connected to the pump volume to form a main fluid channel for transferring the medical fluid from the pump volume to a patient; and
   a mechanical monitoring device operatively connected to the infusion line and configured for monitoring the functioning of the pump apparatus, the mechanical monitoring device comprising a differential pressure-measuring element operatively connected to the main fluid channel, the mechanical monitoring device designed such that a differential pressure formed along a channel portion of the main fluid channel is detectable by the differential pressure-measuring element and, in a manner dependent on the differential pressure, a delivery rate of the medical fluid along the main fluid channel is able to be indicated,
   the differential pressure-measuring element comprising:
   a first line portion fluidly connected to the main fluid channel;
   a second line portion fluidly connected to the main fluid channel;
   a first mechanical measurement member operatively connected to the first line portion and deflectable in response to fluid pressure in the first line portion;
   a second mechanical measurement member operatively connected to the second line portion and deflectable in response to fluid pressure in the second line portion; and
   a fluid chamber arranged in parallel to the infusion line, the fluid chamber containing a fluid that is separate and distinct from the medical fluid, the fluid chamber positioned between and hydraulically coupled to the first mechanical measurement member and the second mechanical measurement member.

2. The infusion arrangement according to claim 1, wherein the mechanical monitoring device has a bypass channel which is operatively connected at one end by means of a first channel branch, and at the other end by means of a second channel branch, to the main fluid channel, in each case in fluid pressure-transmitting fashion, wherein the differential pressure-measuring element is arranged in the bypass channel.

3. The infusion arrangement according to claim 1, wherein the first mechanical measurement member and the second mechanical measurement member are deflectable in resiliently elastic fashion.

4. The infusion arrangement according to claim 1, wherein at least one of the first mechanical measurement member and the second mechanical measurement member has a resiliently elastic membrane.

5. The infusion arrangement according to claim 1, wherein the mechanical monitoring device has an indicator element which is operatively connected to the differential pressure-measuring element and which is configured for indicating the delivery rate in a manner dependent on the differential pressure.

6. The infusion arrangement according to claim 5, wherein the indicator element is arranged in the fluid chamber so as to be movable in a floating manner.

7. The infusion arrangement according to claim 6, wherein the indicator element is in the form of a float or of a dyed oil drop.

8. The infusion arrangement according to claim 2, wherein the mechanical monitoring device has a first fluid-throttling element arranged in the main fluid channel between the first channel branch and the second channel branch.

9. The infusion arrangement according to claim 8, wherein a second fluid-throttling element is arranged in the main fluid channel downstream of the second channel branch.

10. The infusion arrangement according to claim 9, wherein the first fluid-throttling element has a throttling action which is lower in comparison with the second fluid-throttling element.

11. An infusion arrangement for administering a medical fluid comprising:

a medical pump apparatus comprising an elastomeric membrane which forms a pump volume for receiving and delivering the medical fluid;

an infusion line configured to be operatively connected to the pump volume to form a main fluid channel for transferring the medical fluid from the pump volume to a patient; and a mechanical monitoring device operatively connected to the infusion line and configured for monitoring the functioning of the pump apparatus, the mechanical monitoring device comprising a differential pressure-measuring element operatively connected to the main fluid channel, the differential pressure-measuring element configured to detect a differential pressure formed along a channel portion of the main fluid channel and, in a manner dependent on the differential pressure, indicate a delivery rate of the medical fluid along the main fluid channel, the differential pressure-measuring element comprising:

a first line portion fluidly connected to the main fluid channel;

a second line portion fluidly connected to the main fluid channel;

a first mechanical measurement member operatively connected to the first line portion and deflectable in response to fluid pressure in the first line portion;

a second mechanical measurement member operatively connected to the second line portion and deflectable in response to fluid pressure in the second line portion; and a fluid chamber containing a fluid that is separate and distinct from the medical fluid, the fluid chamber positioned between and hydraulically coupled to the first mechanical measurement member and the second mechanical measurement member.

12. The infusion arrangement according to claim 11, wherein the mechanical monitoring device has a bypass channel which is operatively connected at one end by means of a first channel branch, and at the other end by means of a second channel branch, to the main fluid channel, in each case in fluid pressure-transmitting fashion, wherein the differential pressure-measuring element is arranged in the bypass channel.

13. The infusion arrangement according to claim 11, wherein the first mechanical measurement member and the second mechanical measurement member are deflectable in resiliently elastic fashion.

14. The infusion arrangement according to claim 11, wherein at least one of the first mechanical measurement member and the second mechanical measurement member has a resiliently elastic membrane.

15. The infusion arrangement according to claim 11, wherein the mechanical monitoring device has an indicator element which is operatively connected to the differential pressure-measuring element and which is configured for indicating the delivery rate in a manner dependent on the differential pressure.

16. The infusion arrangement according to claim 15, wherein the indicator element is arranged in the fluid chamber so as to be movable in a floating manner.

17. The infusion arrangement according to claim 16, wherein the indicator element is in the form of a float or of a dyed oil drop.

18. The infusion arrangement according to claim 12, wherein the mechanical monitoring device has a first fluid-throttling element arranged in the main fluid channel between the first channel branch and the second channel branch.

19. The infusion arrangement according to claim 18, wherein a second fluid-throttling element is arranged in the main fluid channel downstream of the second channel branch.

20. An infusion arrangement for administering a medical fluid comprising:

a medical pump apparatus comprising a membrane which forms a pump volume for receiving and delivering the medical fluid;

an infusion line configured to be operatively connected to the pump volume to form a main fluid channel for transferring the medical fluid from the pump volume to a patient; and a mechanical monitoring device operatively connected to the infusion line, the mechanical monitoring device comprising a differential pressure-measuring element operatively connected to the main fluid channel, the differential pressure-measuring element configured to detect a differential pressure formed along a channel portion of the main fluid channel and, in a manner dependent on the differential pressure, indicate a delivery rate of the medical fluid along the main fluid channel, the differential pressure-measuring element comprising:

a first line portion fluidly connected to the main fluid channel;

a second line portion fluidly connected to the main fluid channel;

a first mechanical measurement member deflectable in response to fluid pressure in the first line portion;

a second mechanical measurement member deflectable in response to fluid pressure in the second line portion; and a fluid chamber containing a fluid that is separate and distinct from the medical fluid, the fluid chamber positioned between and hydraulically coupled to the first mechanical measurement member and the second mechanical measurement member.

* * * * *